United States Patent
Yoon et al.

(10) Patent No.: US 7,169,879 B2
(45) Date of Patent: Jan. 30, 2007

(54) BISPHENYL-2,3,5,6-TETRAFLUORO-4-TRIFLUOROMETHYLPHENYL PHOSPHINE OXIDE DERIVATIVE AND SYNTHESIS THEREOF

(75) Inventors: Tae-Ho Yoon, Gwangju (KR); Chul Woong Lee, Gwangju (KR); Sang Min Kwak, Gwangju (KR)

(73) Assignee: Gwangju Institute of Science and Technology, Gwangju (KR)

( * ) Notice: Subject to any disclaimer, the term of this patent is extended or adjusted under 35 U.S.C. 154(b) by 90 days.

(21) Appl. No.: 11/016,293

(22) Filed: Dec. 17, 2004

(65) Prior Publication Data

US 2005/0267317 A1   Dec. 1, 2005

(30) Foreign Application Priority Data

May 28, 2004   (KR) .................... 10-2004-0038476

(51) Int. Cl.
    *C08C 73/00*   (2006.01)
(52) U.S. Cl. .................... 528/170; 528/310; 568/14
(58) Field of Classification Search .............. 568/14; 528/170, 310
    See application file for complete search history.

(56) References Cited

U.S. PATENT DOCUMENTS

| | | | | |
|---|---|---|---|---|
| 5,482,596 A | * | 1/1996 | Wu | 562/406 |
| 5,703,269 A | * | 12/1997 | Herrmann et al. | 560/19 |
| 5,902,898 A | * | 5/1999 | Wu | 562/406 |
| 6,194,627 B1 | * | 2/2001 | Geissler et al. | 585/436 |

OTHER PUBLICATIONS

Martinez-Nuez et al., Polymer Preprint, 35:709 (1994).

* cited by examiner

*Primary Examiner*—Thurman K. Page
*Assistant Examiner*—Chukwuma Nwaonicha
(74) *Attorney, Agent, or Firm*—Peter F. Corless; Edwards Angell Palmer & Dodge LLP

(57) ABSTRACT

The present invention relates to bisphenyl-2,3,5,6-tetrafluoro-4-trifluoromethylphenylphosphine oxide compounds and synthesis thereof, more particularly to novel bisphenyl-2,3,5,6-tetrafluoro-4-trifluoromethylphenylphosphine oxide compounds having both a perfluorinated benzene substituent and a phosphine oxide moiety. Compounds of the invention can be useful as a monomer for preparing polyimides having a low dielectric constant and a superior adhesion while maintaining the superior thermal and mechanical properties of polyimides themselves, and their synthesis thereof.

3 Claims, 6 Drawing Sheets

Solvent : DMSO-d$_6$

BISPHENYL-2,3,5,6-TETRAFLUORO-4-TRIFLUOROMETHYLPHENYL PHOSPHINE OXIDE DERIVATIVE AND SYNTHESIS THEREOF

CROSS-REFERENCE TO RELATED APPLICATIONS

This application is based on, and claims priority from Korean Patent Application No. 2004-0038476, filed on May 28, 2004, the disclosure of which is hereby incorporated by reference.

BACKGROUND OF THE INVENTION

1. Field of the Invention

The present invention relates to bisphenyl-2,3,5,6-tetrafluoro-4-trifluoromethylphenylphosphine oxide compounds and synthesis thereof, more particularly to novel bisphenyl-2,3,5,6-tetrafluoro-4-trifluoromethylphenylphosphine oxide compounds having both a perfluorinated benzene substituent and phosphine oxide moiety, which is useful as a monomer for preparing polyimides having a low dielectric constant and a superior adhesion while maintaining the superior thermal and mechanical properties of polyimides themselves, and a synthesis thereof.

2. Background

Polyimides have a wide scope of applications as materials for electronic products, molding products, heat-resistant adhesives, and insulation due to their superior insulating properties, thermal stability at high temperature, glass transition temperature, heat resistance, chemical resistance, mechanical property, etc. compared with other conventional organic polymers. Further, the superior thermal and chemical stabilities as well as low dielectric constant of the polyimides have extended their use even as a material for preparing inter-layer insulating films and protection films of semiconductor chips. However, the polyimides developed so far are still not sufficient to be used for manufacturing gigabyte (GB) level integration chips, and thus there has been an urgent need to develop polyimides with much improved processability and lower dielectric constant.

Recent studies have revealed that fluorine compounds, due to their superior processability, low hygroscopy, low dielectric constant and good chemical stability, can improve solubility, electrical insulation, and chemical resistance. This is because each fluorine atom has small van der Waals radius, highest electronegativity, large binding energy with other elements, thus reducing surface tension by decreasing intermolecular attraction. Therefore, various kinds of monomers containing fluorine compounds have been developed in order to obtain polyimides having superior processability and low dielectric constant while maintaining their superior thermal and mechanical properties. Further, fluorine-containing polyimides are widely used in high-precision electronics industries such as manufacturing high integration connecting device packages.

For polyimides to be used as electronics materials, especially as those for manufacturing semiconductor chips, it is essential for them to have superior adhesion in addition to superior thermal and mechanical stabilities and low dielectric constant. However, fluorine-containing polyimides in general have relatively low adhesion, and to overcome this defect, there have been developed polyimides containing phosphine oxide, which are known effective in improving adhesion and flame retardancy, in addition to fluorine. Bis(3-aminophenyl)phenylphosphine oxide (DAPPO) developed by Professor J. E. McGrath and his colleagues of Virginia Tech., U.S. is a good example [M. F. Martinez-Nuez et al., *Polymer Preprint*, 35, p. 709 (1994)].

As stated above, polyimides, which have superior thermal stability and superior mechanical and electrical properties, should also have sufficient adhesion and low dielectric constant to be used as materials for manufacturing high integration electronics devices with multi-layered structures. Therefore, there has been a long-felt need for the development of monomers for efficiently synthesizing such polyimides.

SUMMARY OF THE INVENTION

The invention provides new compositions that contain a perfluorinated benzene substituent and phosphine oxide moiety. Further, polyimides obtainable or produced by polymerization of one or more compounds of the invention are provided. Particularly preferred polyimides of the invention can exhibit superior adhesion and low dielectric constant while retaining other advantageous properties associated with polyimide materials.

Accordingly, it is an aspect of the present invention to provide a bisphenyl-2,3,5,6-tetrafluoro-4-trifluoromethylphenylphosphine oxide derivative and a method of its synthesis.

Further, it is another aspect of the present invention to provide polyimides prepared from imide polymerization of the bis(3-aminophenyl)-2,3,5,6-tetrafluoro-4-trifluoromethylphenylphosphine oxide derivative and a dianhydride monomer.

Other aspects of the invention are discussed below.

BRIEF DESCRIPTION OF THE DRAWINGS

The aforementioned aspects and other features of the present invention will be explained in the following description, taken in conjunction with the accompanying drawings, wherein.

DETAILED DESCRIPTION OF THE PREFERRED EMBODIMENTS

Figure 1:
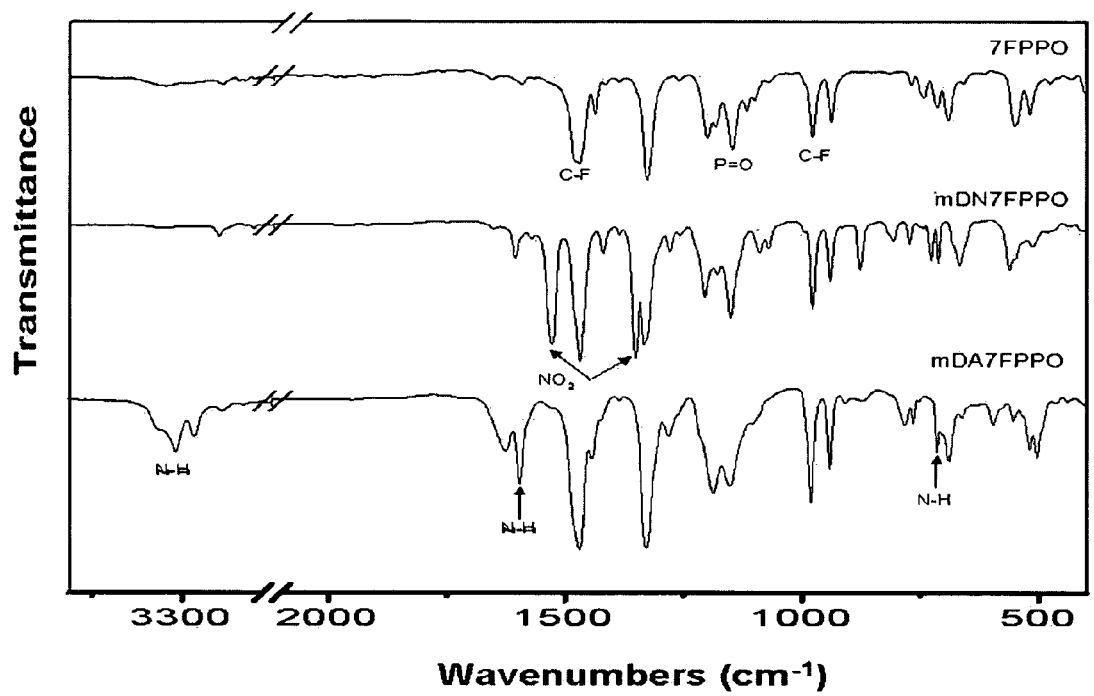
FIG. 1 shows a result of FT-IR analysis for 2,3,5,6-tetrafluoro-4-trifluoromethylphenyldiphenylphosphine oxide (7FPPO), bis(3-nitrophenyl)-2,3,5,6-tetrafluoro-4-trifluoromethylphenylphosphine oxide (DN7FPPO) and bis(3-aminophenyl)-2,3,5,6-tetrafluoro-4-trifluoromethylphenylphosphine oxide (DA7FPPO)

The present invention relates to bisphenyl-2,3,5,6-tetrafluoro-4-trifluoromethylphenylphosphine oxide compounds represented by Formula 1 below, which is substituted by a perfluorinated benzene substituent and a phosphine oxide:

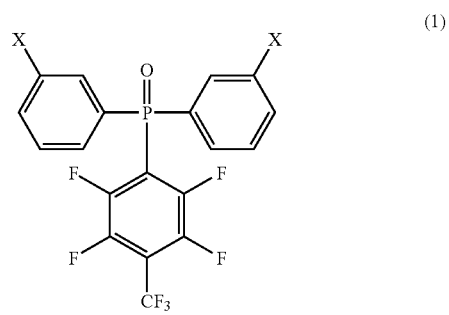

wherein each X independently represents a hydrogen atom, a nitro group or an amine group.

Hereunder is given a more detailed description of the present invention.

The bisphenyl-2,3,5,6-tetrafluoro-4-trifluoromethylphenylphosphine oxide derivative represented by Formula 1 contains phosphine oxide and perfluorinated benzene moieties. Hence, a polymer prepared from the derivative, including polyimides, should be provided with superior solubility, low dielectric constant, low hygroscopy, and superior adhesion so that it can be used in manufacturing electronics devices.

The present invention also provides methods of preparing compounds represented by Formula 1. Particularly preferred preparation methods of the invention are illustrated by the following exemplary Scheme 1:

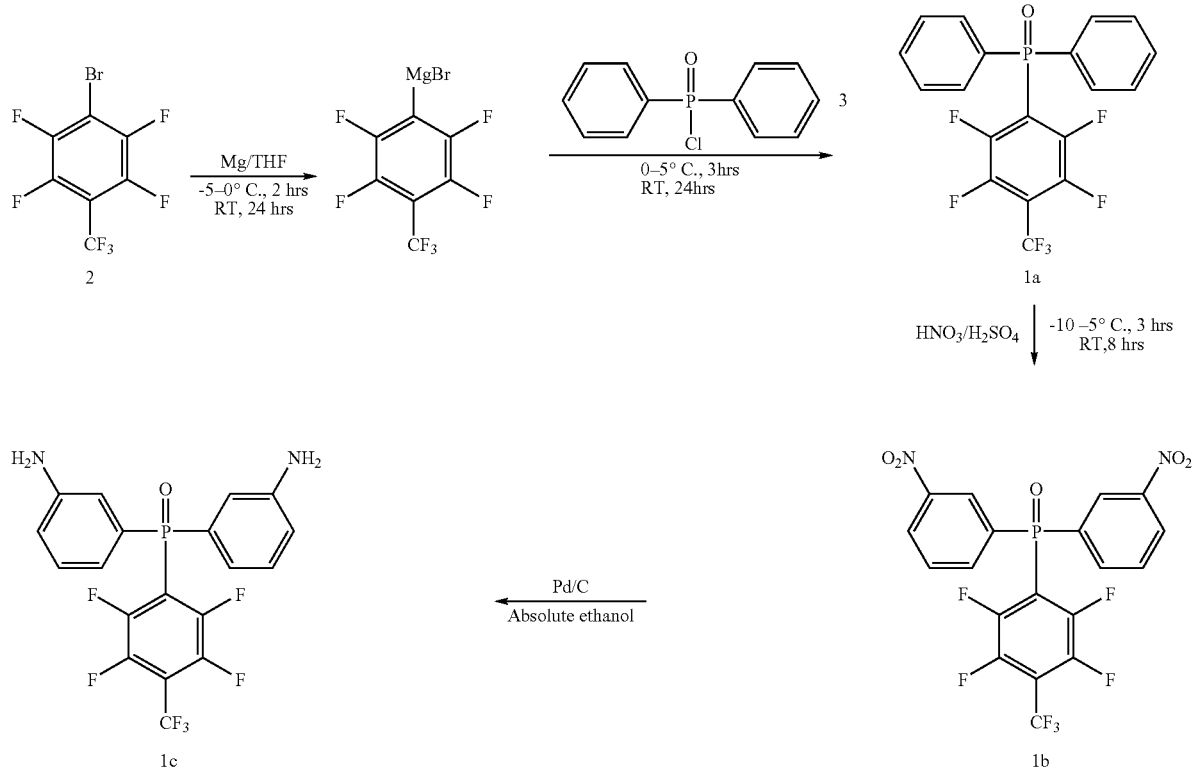

The method according to Scheme 1 comprises:

a) performing a Grignard reaction of the 2,3,5,6-tetrafluoro-4-trifluoromethylbromobenzene represented by Formula 2 and the diphenylphosphonic chloride represented by Formula 3 in the presence of an organic solvent and magnesium to obtain the 2,3,5,6-tetrafluoro-4-trifluoromethylphenyldiphenylphosphine oxide (7FPPO) represented by Formula 1a;

b) nitrating the compound represented by Formula 1a (7FPPO) with sulfuric acid and nitric acid to obtain the bis(3-nitrophenyl)-2,3,5,6-tetrafluoro-4-trifluoromethylphenylphosphine oxide (DN7FPPO) represented by Formula 1b; and c) hydrogenating the compound represented by Formula 1b (DN7FPPO) in the presence of a palladium catalyst to obtain the bis(3-aminophenyl)-2,3,5,6-tetrafluoro-4-trifluoromethylphenylphosphine oxide (DA7FPPO) represented by Formula 1c.

Hereinafter, the synthesis according to Scheme 1 is described in greater detail.

First, the compound represented by Formula 2 is reacted in the presence of magnesium powder and an organic solvent to prepare a Grignard reagent. This reaction is suitably performed at −5 to 0° C. for 3 to 4 hr, and then at room temperature for 24 hr while stirring. Then, the Grignard reagent is reacted with the diphenylphosphonic chloride represented by Formula 4 (Grignard reaction) to obtain the compound represented by Formula 1a (7FPPO). The Grignard reagent is used in the amount of 1 to 1.2 moles and the reaction is performed at 0 to 5° C. for 3 to 4 hr, and then at room temperature for 24 hr while stirring.

Then, the compound represented by Formula 1a (7FPPO) is nitrated using sulfuric acid and nitric acid to obtain the dinitro compound represented by Formula 1b (DN7FPPO). The nitration is suitably performed at −5 to −10° C. for 2 to 3 hr, and then at 10 to 30° C. for 5 to 10 hr while stirring.

Then, the dinitro compound represented by Formula 1b (DN7FPPO) is hydrogenated in the presence of a palladium catalyst (Pd/C) using absolute ethanol as organic solvent to obtain the diamine compound represented by Formula 1c (DA7FPPO). The hydrogenation is suitably performed under 40 to 150 psi of hydrogen pressure and at 30 to 70° C. for 12 to 36 hr. Differing X groups in Formula I can be readily provided, e.g. by hydrogenating under varying conditions, including using varying catalysts (e.g. poisoned catalyst) or higher pressures and/or temperatures. For at least certain applications, however, the X substituents of a compound of Formula I will be the same and not different.

The diamine compound represented by Formula 1c is a useful monomer to be used in polymerization. Examples of polymers produced by the polymerization of the diamine compounds are polyimides, polyamides, polysulfones and copolymers thereof and they can be prepared by using the conventional method of polymerization.

Scheme 2 below is an exemplary method of polyimide synthesis using the diamine compound represented by Formula 1c (DA7FPPO) and a common dianhydride monomer:

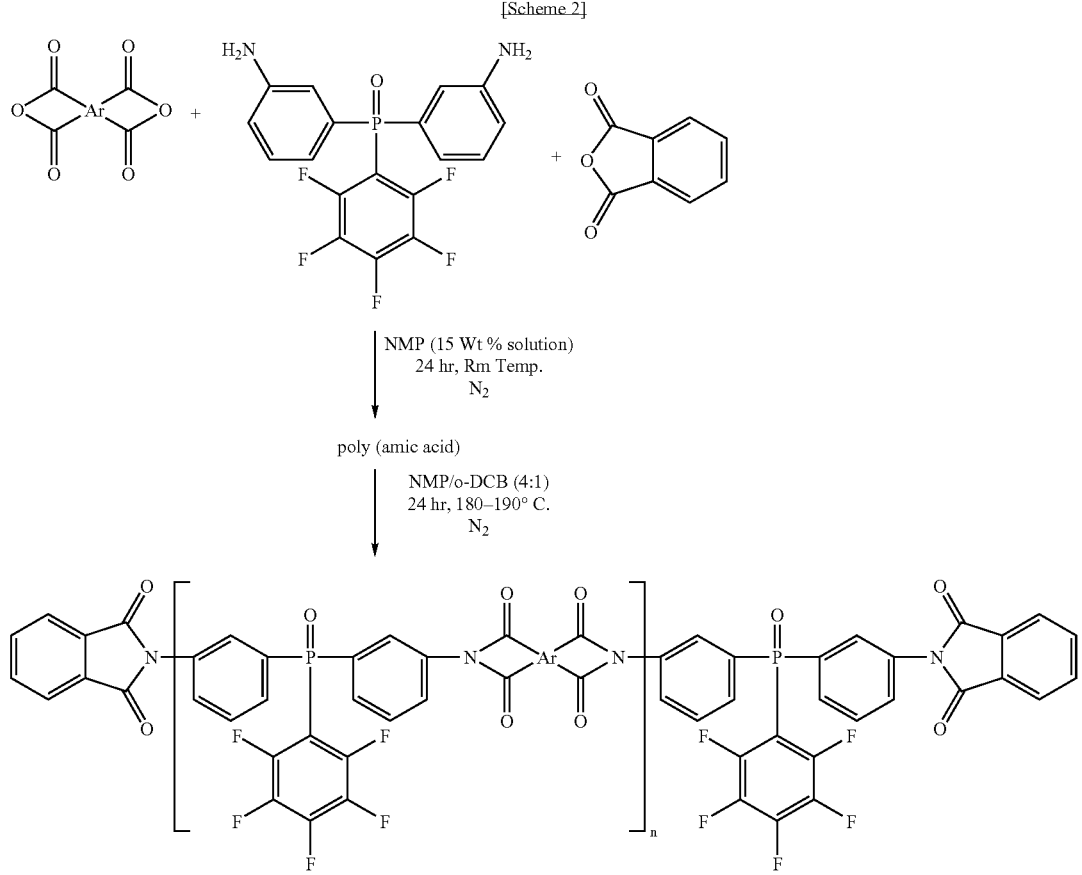

wherein Ar represents an aliphatic or aromatic ring such as cyclohexyl, phenyl, naphthyl and the like.

When synthesizing polyimides via polymerization of a diamine monomer and an aliphatic or aromatic dianhydride monomer, as in Scheme 2, the target compound having desirable properties can be easily obtained via solution imidization using the compound represented by Formula 1c as the diamine monomer.

The dianhydride monomer may be a common aliphatic or aromatic dianhydride used in synthesis of polyimides, such as 2,2-bis(3,4-dicarboxyphenyl)hexafluoropropane dianhydride (6FDA), 3,3',4,4'-benzophenonetetracarboxylic dianhydride (BTDA) and 4,4'-oxydiphthalic anhydride (ODPA).

Hereinafter, the present invention is described in more detail in the following examples. However, they are only for the understanding of the present invention and therefore they should not be construed as limiting the scope of the present invention.

EXAMPLES

Example 1

Preparation of 2,3,5,6-tetrafluoro-4-trifluoromethylphenyldiphenylphosphine oxide (7FPPO, Formula 1a)

A 500 mL 3-necked round bottom flask equipped with a magnetic stirrer, a dropping funnel, a condenser and a nitrogen inlet was prepared. 1.47 g of magnesium (Mg) powder (Aldrich) and 150 mL of distilled tetrahydrofuran (THF) (Aldrich) were added to the reactor. The reaction mixture was cooled to −5° C. or below in an ice/salt bath. Then, 15 g of 2,3,5,6-tetrafluoro-4-trifluoromethylbromobenzene (Fluorochem) was slowly added for about 3 hr using a dropping funnel and the reaction solution was allowed to reach room temperature. A reaction was then performed at room temperature for 24 hr to obtain 2,3,5,6-tetrafluoro-4-trifluoromethylphenyl magnesium bromide, which is a Grignard reagent.

The reaction product was cooled to −5° C. or below using an ice/salt bath. 11.9 g of diphenylphosphonic chloride (Aldrich) was slowly added for about 3 hr to the cooled reaction product using the dropping funnel. The reaction product was allowed to reach room temperature. Reaction was then performed at room temperature for 24 hr to obtain a dark brown solution. 100 mL of 10% sulfuric acid solution was added to the reaction product to terminate the reaction. After washing with 1 L of water, the reaction product was neutralized with sodium bicarbonate ($NaHCO_3$) and extracted using diethyl ether and water. The extract was recrystallized using 2 L of boiling hexane to obtain 17.1 g of bis(3-nitrophenyl)-2,3,5,6-tetrafluoro-4-trifluoromethylphenylphosphine oxide (yield: 81%).

Figure 2:
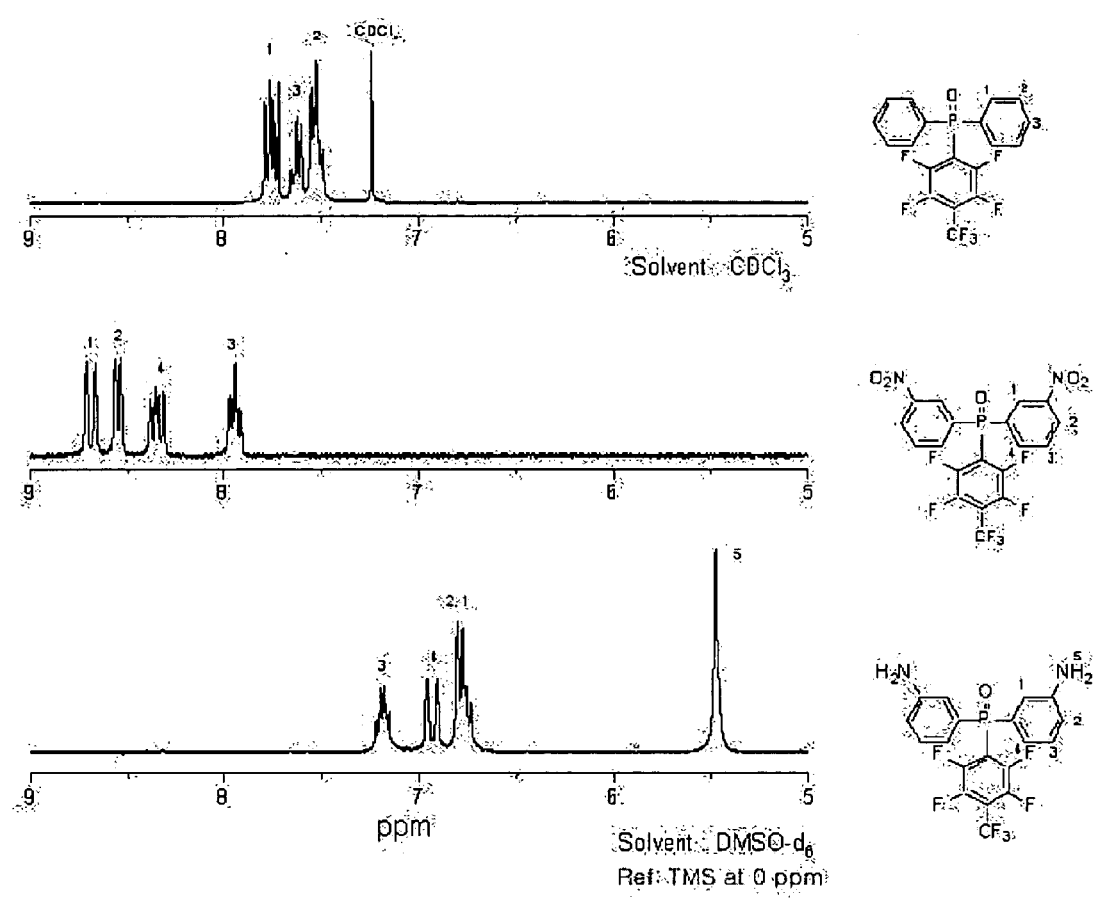
FIG. 2 shows a result of $^1$H-NMR analysis for 2,3,5,6-tetrafluoro-4-trifluoromethylphenyldiphenylphosphine oxide (7FPPO), bis(3-nitrophenyl)-2,3,5,6-tetrafluoro-4-trifluoromethylphenylphosphine oxide (DN7FPPO) and bis(3-aminophenyl)-2,3,5,6-tetrafluoro-4-trifluoromethylphenylphosphine oxide (DA7FPPO)
Figure 3:
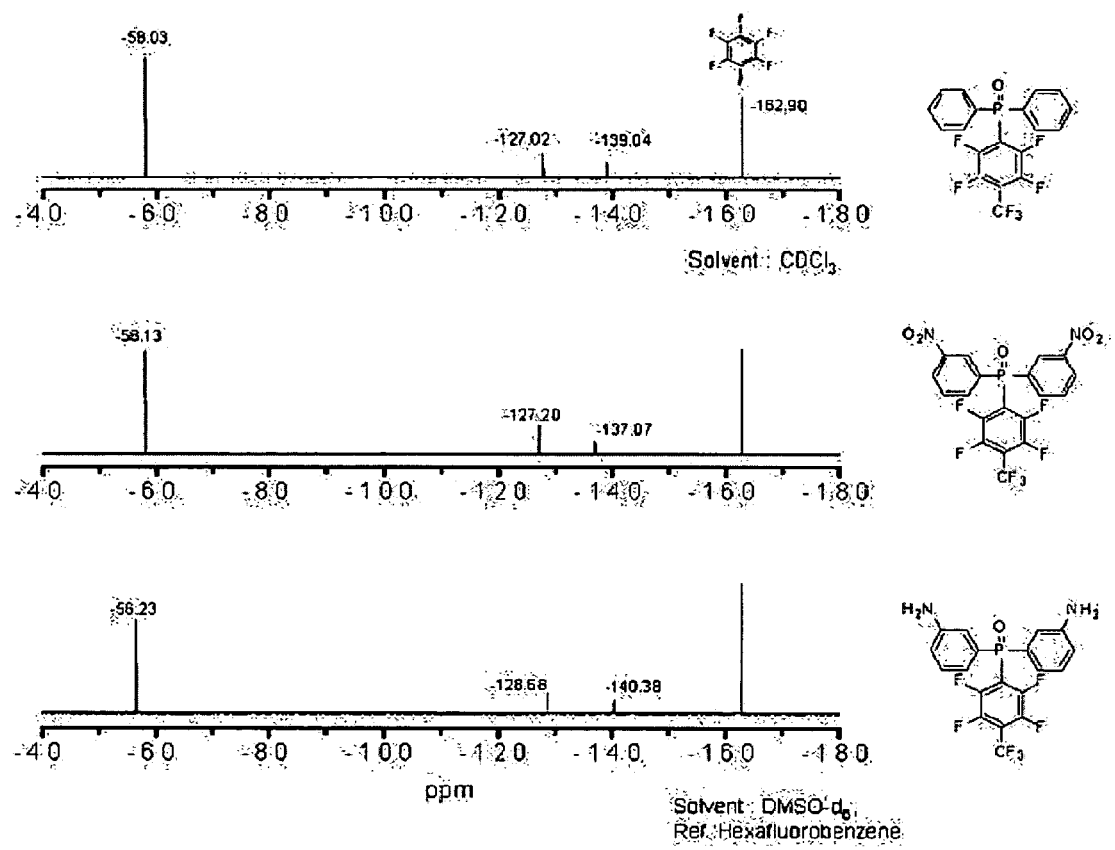
FIG. 3 shows a result of $^{19}$F-NMR analysis for 2,3,5,6-tetrafluoro-4-trifluoromethylphenyldiphenylphosphine oxide (7FPPO), bis(3-nitrophenyl)-2,3,5,6-tetrafluoro-4-trifluoromethylphenylphosphine oxide (DN7FPPO) and bis(3-aminophenyl)-2,3,5,6-tetrafluoro-4-trifluoromethylphenylphosphine oxide (DA7FPPO)
Figure 4:
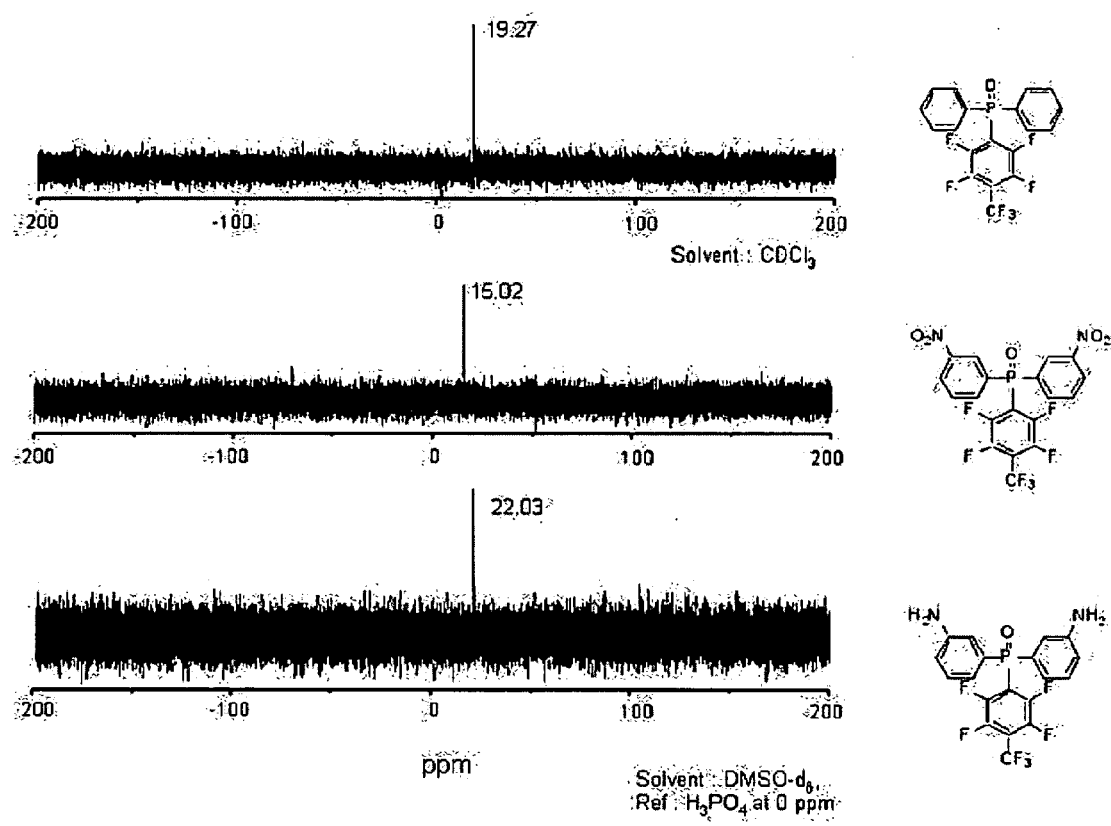
FIG. 4 shows a result of $^{31}$P-NMR analysis for 2,3,5,6-tetrafluoro-4-trifluoromethylphenyldiphenylphosphine oxide (7FPPO), bis(3-nitrophenyl)-2,3,5,6-tetrafluoro-4-trifluoromethylphenylphosphine oxide (DN7FPPO) and bis(3-aminophenyl)-2,3,5,6-tetrafluoro-4-trifluoromethylphenylphosphine oxide (DA7FPPO)

The obtained compound (7FPPO) was dried in a vacuum oven of 40° C. for 12 hr and characterized by measuring its melting point and FT-IR, $^1$H-NMR, $^{19}$F-NMR and $^{31}$P-NMR analyses. The melting point ranged from 115.4 to 116.1° C. The FT-IR analysis revealed a P=O stretching peak at 1,195 $cm^{-1}$ and a C—F peak in between 1,100 and 1300 $cm^{-1}$ (see FIG. 1). The $^1$H-NMR analysis (solvent: $CDCl_3$) revealed diphenyl $^1$H peaks at 7.76 ppm, 7.62 ppm and 7.52 ppm (see FIG. 2). The $^{19}$F-NMR analysis (solvent: $CDCl_3$) revealed peaks of $^{19}$F attached to phenyl ring at −127.02 ppm and −139.04 ppm and peaks of $^{19}$F substituted as $CF_3$ for a methyl at −58.03 ppm (see FIG. 3). The $^{31}$P-NMR analysis (solvent: $CDCl_3$) revealed a single peak at 19.27 ppm (see FIG. 4). These analyses clearly demonstrated successful preparation of the target compound.

Example 2

Preparation of bis(3-nitrophenyl)-2,3,5,6-tetrafluoro-4-trifluoromethylphenylphosphine oxide (DN7FPPO, Formula 1b)

A 250 mL 3-necked round bottom flask equipped with a magnetic stirrer, a dropping funnel, a condenser and a nitrogen inlet was prepared. 7 g of the compound synthesized in Example 1 (7FPPO) and 70 mL of sulfuric acid was added. The mixture was dissolved at room temperature for about 30 minutes. The reaction mixture was cooled to −10 to −5° C. using an ice/salt bath. Then, a mixture solution of 2.4 mL of nitric acid and 10.5 mL of sulfuric acid was slowly added for about 2 hr using the dropping funnel. The reaction solution was allowed to reach room temperature and a reaction was then performed at room temperature for 8 hr. After the reaction was completed, the reaction product was mixed with 1 kg of ice water. When the mixture reached room temperature, it was neutralized with sodium bicarbonate ($NaHCO_3$) and extracted using chloroform and water. The extract was recrystallized by dissolving in boiling absolute ethanol to obtain 7.5 g of a dinitro compound (DN7FPPO) (yield: 89%).

The obtained dinitro compound (DN7FPPO) was dried in a vacuum oven of 40° C. for 12 hr. Melting point of the compound was measured and FT-IR, $^1$H-NMR, $^{19}$F-NMR and $^{31}$P-NMR analyses were performed to identify the compound. The melting point ranged from 160.2 to 160.9° C. The FT-IR analysis revealed a an asymmetric stretching peak, which is unique to an aromatic nitro compound, at 1,529 $cm^{-1}$ and a symmetric stretching peak at 1,350 $cm^{-1}$ (see FIG. 1). The $^1$H-NMR analysis (solvent: DMSO-$d_6$) showed four diphenyl peaks at 8.62 ppm, 8.54–8.51 ppm, 8.16 ppm and 7.85 ppm, which confirms the $NO_2$ group (see FIG. 2). The $^{19}$F-NMR analysis (solvent: DMSO-$d_6$) showed a shift of the phenyl $^{19}$F peaks from −127.02 ppm to −127.20 ppm and from −139.04 ppm to −137.07 ppm and shift of the methyl $^{19}$F peak from −58.03 ppm to −58.13 ppm (see FIG. 3). The $^{31}$P-NMR analysis (solvent: DMSO-$d_6$) showed a shift of the peak from 19.27 ppm to 15.02 ppm because of the $NO_2$ group (see FIG. 4). These analyses clearly demonstrated successful preparation of the target compound. Further, the presence of a single peak proves that the obtained product is of high purity.

Example 3

Preparation of bis(3-aminophenyl)-2,3,5,6-tetrafluoro-4-trifluoromethylphenylphosphine oxide (DA7FPPO, Formula 1c)

12 g of the dinitro compound (DN7FPPO) synthesized in Example 2, 150 mL of absolute ethanol and 15 mg of 10% Pd/C were put in a high pressure reactor. Reaction was performed under 100 psi of hydrogen pressure and at 50° C. for 24 hr. The palladium catalyst (Pd/C) was separated from the reaction product using celite. The solvent was evaporated and the reaction product was purified by column chromatography to obtain a diamine compound (DA7FPPO; yield: 83%).

Melting point of the diamine compound (DA7FPPO) was measured and FT-IR, $^1$H-NMR, $^{19}$F-NMR and $^{31}$P-NMR analyses were performed. The melting point ranged from 187.3 to 187.6° C. The FT-IR analysis revealed a primary amine stretching peak in between 3,500 and 3,300 cm$^{-1}$ and a primary amine bending peak at 1,597 cm$^{-1}$ (see FIG. 1). The $^1$H-NMR analysis (solvent: DMSO-d$_6$) showed amine-substituted phenyl $^1$H peaks at 7.22–7.15, 6.92 and 6.80–6.74 ppm and a single amine $^1$H peak at 5.49 ppm (see FIG. 2). The $^{19}$F-NMR analysis (solvent: DMSO-d$_6$) showed a shift of the phenyl $^{19}$F peaks from −127.20 ppm to −128.68 ppm and from −137.07 ppm to −140.38 ppm and shift of the methyl $^{19}$F peak from −58.13 ppm to −56.23 ppm (see FIG. 3). The 31P-NMR analysis (solvent: DMSO-d$_6$) showed a shift from 15.02 ppm to 22.03 ppm (see FIG. 4), which confirmed production of amine. These analyses clearly demonstrated successful preparation of the target compound.

Example 4

Polyimide synthesis using bis(3-aminophenyl)-2,3,5,6-tetrafluoro-4-trifluoromethylphenylphosphine oxide (DA7FPPO, Formula 1c)

A 250 mL 3-necked round bottom flask equipped with a mechanical stirrer, a condenser and a nitrogen inlet was prepared. 6.1 g (13.64 mmol) of the diamine compound (DA7FPPO) synthesized in Example 3 and 50 mL of distilled 1-methyl-2-pyrrolidone (NMP, Fluka) were added to the reactor. After DA7FPPO was completely dissolved, 0.16 g (1.10 mmol) of phthalic anhydride (PA, Aldrich) and 5.82 g (13.09 mmol) of 2,2-bis(3,4-dicarboxyphenyl)hexafluoropropane dianhydride (6FDA, Chriskev) were sequentially added to the reactor. Then, the reaction was then performed at room temperature for 24 hr.

Imidization of poly(amic acid) was performed in a 250 mL 3-necked round bottom flask equipped with a mechanical stirrer, a nitrogen inlet and a Dean-Stark trap. First, 12.5 mL of o-dichlorobenzene (o-DCB, Aldrich) was added and reaction was performed at 170 to 180° C. for 24 hr while under a nitrogen atmosphere. After the reaction was completed, the reaction product was cooled to room temperature, precipitated in water/methanol, and then washed. The obtained polyimide powder was dissolved in chloroform, re-precipitated in water/methanol and filtered to remove NMP. The obtained polyimide was dried for 2 hr at 100° C., for 6 hr at 200° C. and then for 20 minutes at the glass transition temperature of +20° C. The number average molecular weight of the obtained polyimides were controlled to 20,000 g/mol.

FT-IR (IR 2000, Perkin Elmer), $^1$H-NMR (300 MHz, Jeol), $^{31}$P-NMR and $^{19}$F-NMR analyses were performed to identify the structure of the obtained polyimide.

Figure 5:
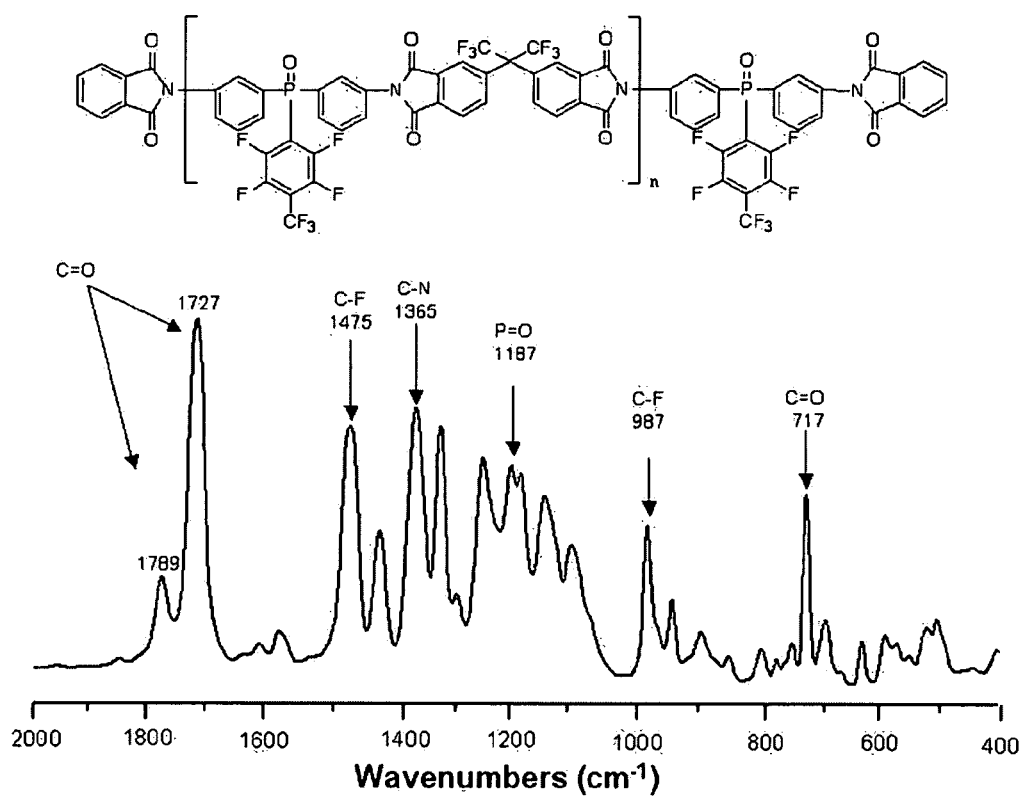
FIG. 5 shows a result of FT-IR analysis for polyimides synthesized from imide polymerization of a diamine monomer of bis(3-aminophenyl)-2,3,5,6-tetrafluoro-4-trifluoromethylphenylphosphine oxide (DA7FPPO) and a 6FDA monomer.

The FT-IR analysis revealed a symmetric C=O peak, which is characteristic of a imide group, at 1,727 cm$^{-1}$), an asymmetric stretching peak at 1,789 cm$^{-1}$ and a C—N stretching peak at 1,365 cm$^{-1}$ (see FIG. 5). Further, a P=O stretching peak at 1,187 cm$^{-1}$, a methyl C—F peak at 1,250–1,092 cm$^{-1}$ and a benzene ring C—F peak at 1,475 cm$^{-1}$ were observed.

Figure 6:
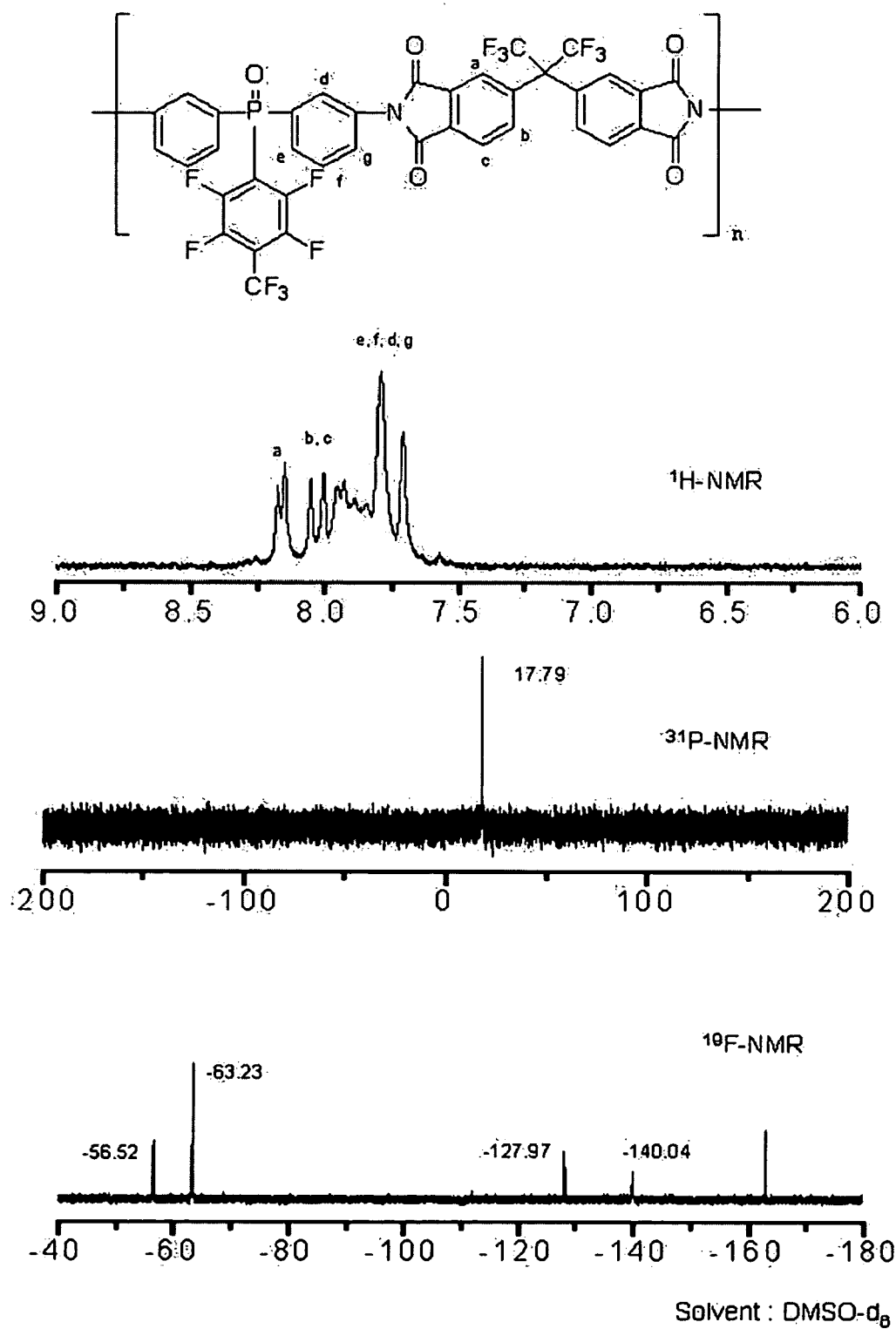
FIG. 6 shows results of $^1$H-NMR, $^{19}$F-NMR and $^{31}$P-NMR analyses for polyimides synthesized from imide polymerization of a diamine monomer of bis(3-aminophenyl)-2,3,5,6-tetrafluoro-4-trifluoromethylphenylphosphine oxide (DA7FPPO) and a 6FDA monomer.

$^1$H-NMR, $^{31}$P-NMR and $^{19}$F-NMR analyses results are given in FIG. 6. The $^1$H-NMR spectrum of the polyimide (6FDA-DA7FPPO) showed seven $^1$H peaks. Considering the electron withdrawing properties of CF$_3$>imide>P=O, the most deshielded $^1$H peak was assigned to the $^1$H between CF$_3$ and imide (8.3 ppm). The two $^1$H peaks at 8.2 and 7.9 ppm were assigned to the $^1$H present in the phenyl ring of 6FDA. Likewise, the $^1$H peak at 7.75 ppm was assigned to the $^1$H peak present in the phenyl ring of DA7FPPO. The $^{19}$F-NMR (solvent: CDCl$_3$) spectrum showed phenyl $^{19}$F peaks at −127.97 ppm and −140.04 ppm and a methyl $^{19}$F peak at −56.52 ppm. Further, a $^{19}$F peak substituted at 6FDA was observed at −63.23 ppm. The $^{31}$P-NMR spectrum showed a single peak at 17.79 ppm. Consequently, it was identified that polyimides containing a single kind of phosphine were synthesized.

Physical properties of thus synthesized polyimides were measured. The results are presented in Tables 1–3 below.

Intrinsic viscosity measured with a Cannon-Ubbelohde viscometer, molecular weight measured by GPC (Waters, M77251, M510), glass transition temperature measured by DSC (TA-2910) and decomposition temperature measured by TGA (TA-2980) are given in Table 1 below.

TABLE 1

| Diamine | Dianhydride | Intrinsic viscosity (dL/g) | Number average molecular weight | Glass transition temperature (° C.) | Thermal decomposition temperature (° C.) | | Remaining amount (wt %) | |
|---|---|---|---|---|---|---|---|---|
| | | | | | In air | In nitrogen | In air | In nitrogen |
| DA7FPPO | ODPA | 0.22 | 19,200 | 228 | 517 | 523 | 7 | 55 |
| | BTDA | 0.25 | 18,300 | 247 | 511 | 523 | 12 | 58 |
| | 6FDA | 0.25 | 21,100 | 257 | 504 | 515 | 7 | 47 |

The intrinsic viscosity (η) was 0.25 dL/g for BTDA/DA7FPPO, 0.25 dL/g for 6FDA/DA7FPPO and 0.22 dL/g for ODPA/DA7FPPO. The number average molecular weight (M$_n$) of the polyimides measured by GPC were 18,300 g/mol for BTDA/DA7FPPO, 21,100 g/mol for 6FDA/DA7FPPO and 19,200 g/mol for ODPA/DA7FPPO. The intrinsic viscosity and the molecular weight confirm that molecular weight adjustment of the synthesized polyimide was successful. The glass transition temperature (T$_g$) of the polyimide measured by DSC was 257° C. for 6FDA/DA7FPPO, 247° C. for BTDA/DA7FPPO and 228° C. for ODPA/DA7FPPO. The tendency of the glass transition temperature almost coincides with the chain stiffness of the dianhydride (6FDA>BTDA>ODPA). All the polyimides showed superior thermal stability at the TGA test, with thermal decomposition temperature higher than 500° C. (BTDA/DA7FPPO: 511° C., ODPA/DA7FPPO: 517° C. in air) 6FDA/DA7FPPO showed a relatively low decomposition temperature (T$_d$) of 504° C. It appears to be due to the fluorine (F) of the trifluoromethyl group present in 6FDA.

Each prepared polyimide film was immersed in an organic solvent and left at room temperature for 24 hr to measure the solubility of the polyimide. As shown in Table 2 below, all the polyimides were completely dissolved in polar solvents.

TABLE 2

| Classification | | NMP | DMAc | TCE | CHCl₃ | THF | Toluene | Acetone |
|---|---|---|---|---|---|---|---|---|
| DA7FPPO | 6FDA | Dissolved | Dissolved | Dissolved | Dissolved | Dissolved | Not dissolved | Partially dissolved |
| | BTDA | Dissolved | Dissolved | Dissolved | Dissolved | Dissolved | Dissolved | Not dissolved |
| | ODPA | Dissolved | Dissolved | Dissolved | Dissolved | Dissolved | Partially dissolved | Not dissolved |

Dielectric constant (∈) measured with a HP capacitance meter (1 MHz), refractive index measured with a Metricon prism coupler and birefringence calculated from the refractive index are given in Table 3 below.

TABLE 3

| Classification | | Fluorine content (wt %) | Dielectric constant | Refractive index | | Birefringence |
|---|---|---|---|---|---|---|
| | | | | $n_{TE}$ | $n_{TM}$ | |
| DA7FPPO | 6FDA | 28.84 | 2.65 | 1.5209 | 1.5190 | 0.0019 |
| | BTDA | 18.06 | 2.81 | 1.5800 | 1.5751 | 0.0049 |
| | ODPA | 18.36 | 2.77 | 1.5806 | 1.5772 | 0.0034 |

Dielectric constant measured at 1 MHz was low (2.65 for 6FDA/DA7FPPO, 2.81 for BTDA/DA7FPPO and 2.77 for ODPA/DA7FPPO) as expected. 6FDA/DA7FPPO showed the lowest dielectric constant. It appears because the trifluoromethyl group of 6FDA has the highest fluorine content.

Refractive index was also low ($\eta_{TE}$=1.5209 and $\eta_{TM}$=1.5190 for 6FDA/DA7FPPO; $\eta_{TE}$=1.5800 and $\eta_{TE}$=1.5751 for BTDA/DA7FPPO; $\eta_{TE}$=1.5806 and $\eta_{TM}$=1.5772 for ODPA/DA7FPPO). Birefringence calculated from the refractive index very low (0.0019 for 6FDA/DA7FPPO, 0.0049 for BTDA/DA7FPPO and 0.0034 for ODPA/DA7FPPO).

Birefringence (Δη)=$\eta_{TE}$−$\eta_{TM}$ wherein $\eta_{TE}$ is the in-plane refractive index and $\eta_{TM}$ is the out-of-plane refractive index.

The bisphenyl-2,3,5,6-tetrafluoro-4-trifluoromethylphenylphosphine oxide derivative of the present invention, which is represented by Formula 1, is a novel compound having a perfluorinated benzene substituent and a phosphine oxide moiety and is a very useful monomer for polymerizing polyimides.

Of the derivatives represented by Formula 1, the diamine compound offers superior flame retardancy and low dielectric constant to polyimides, when polymerized with the common dianhydride monomer, while maintaining the excellent properties of polyimides such as superior thermal stability and mechanical property. The resultant polyimides can be utilized as a semiconductor packaging material, an inter-layer insulating material of a high integration device, an inter-layer adhesive for metals, etc.

While the present invention has been described in detail with reference to the preferred embodiments, those skilled in the art will appreciate that various modifications and substitutions can be made thereto without departing from the spirit and scope of the present invention as set forth in the appended claims.

All documents mentioned herein are fully incorporated herein by reference.

What is claimed is:

1. A bisphenyl-2,3,5,6-tetrafluoro-4-trifluoromethylphenylphosphine oxide derivative represented by the following Formula 1:

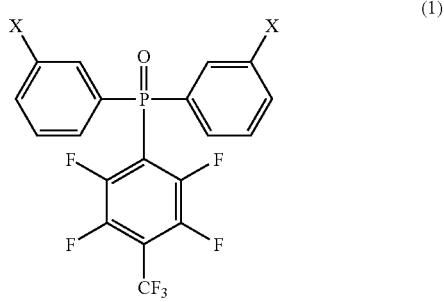

wherein each X independently represents a hydrogen atom, a nitro group or an amine group.

2. A polymer obtainable by reaction comprising imide polymerization of the diamine monomer represented by the following Formula 1c with a dianhydride monomer:

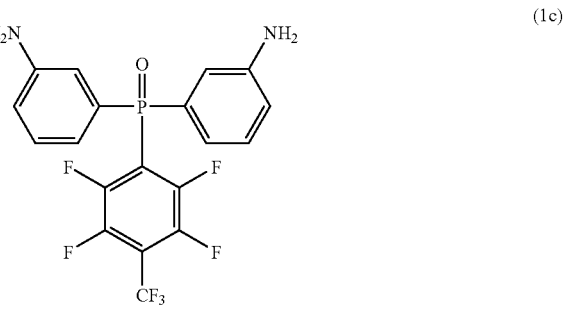

3. A method of preparing a bisphonyl-2,3,5,6-tetrafluoro-4-trifluoromethylphenylphosphine oxide compound comprising:
   a) performing a Grignard reaction of the 2,3,5,6-tetrafluoro-4-trifluoromethylbromobenzene represented by the following Formula 2 and the diphenylphosphonic chloride represented by the following Formula 3 in the presence of an organic solvent and magnesium to obtain the 2,3,5,6-tetrafluoro-4-trifluoromethylphenyldiphenylphosphine oxide represented by the following Formula 1a;

b) nitrating the compound represented by Formula 1a with sulfuric acid and nitric acid to obtain the bis(3-nitrophenyl)-2,3,5,6-tetrafluoro-4-trifluoromethylphenylphosphine oxide represented by the following Formula 1b; and c) hydrogenating the compound represented by Formula 1b in the presence of a palladium catalyst to obtain the bis(3-aminophenyl)-2,3,5,6-tetrafluoro-4-trifluoromethylphenylphosphine oxide represented by the following Formula 1c:

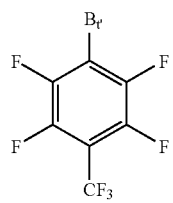

2

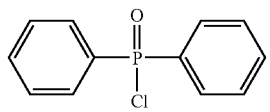

3

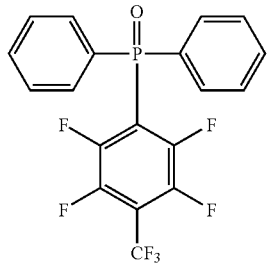

1a

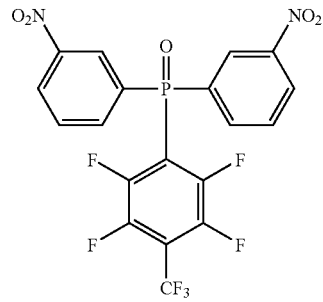

1b

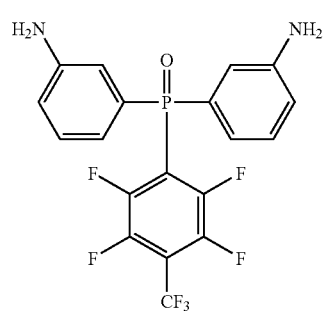

1c

* * * * *